(12) United States Patent
Kühni et al.

(10) Patent No.: US 12,017,048 B2
(45) Date of Patent: Jun. 25, 2024

(54) MONITORING OF DISPOSABLE INJECTION DEVICES

(71) Applicant: Ypsomed AG, Burgdorf (CH)

(72) Inventors: Florian Kühni, Bern (CH); Marc Labudde, Spiegel (CH); Leos Urbanek, Bern (CH)

(73) Assignee: Ypsomed AG, Burgdorf (CH)

( * ) Notice: Subject to any disclaimer, the term of this patent is extended or adjusted under 35 U.S.C. 154(b) by 94 days.

(21) Appl. No.: 16/862,336

(22) Filed: Apr. 29, 2020

(65) Prior Publication Data

US 2020/0261654 A1    Aug. 20, 2020

Related U.S. Application Data

(63) Continuation of application No. PCT/IB2018/058200, filed on Oct. 22, 2018.

(30) Foreign Application Priority Data

Oct. 31, 2017   (EP) .................................. 17199307

(51) Int. Cl.
*A61M 5/31*     (2006.01)
*A61M 5/20*     (2006.01)

(52) U.S. Cl.
CPC ............... *A61M 5/31* (2013.01); *A61M 5/20* (2013.01); *A61M 2005/3125* (2013.01);
(Continued)

(58) Field of Classification Search
CPC .. A61M 5/31; A61M 5/20; A61M 2005/3125; A61M 2205/3553;
(Continued)

(56) References Cited

U.S. PATENT DOCUMENTS 9,552,052 B2    1/2017 Bernstein et al.
2005/0145010 A1    7/2005 Vanderveen et al.
(Continued)

FOREIGN PATENT DOCUMENTS

CN    101184518 A    5/2008
CN    105536095 A    5/2016
(Continued)

OTHER PUBLICATIONS

International Preliminary Report on Patentability received for International Application No. PCT/IB2018/058198, dated May 5, 2020, 8 pages.
(Continued)

*Primary Examiner* — Lauren P Farrar
(74) *Attorney, Agent, or Firm* — Dorsey & Whitney LLP

(57) ABSTRACT

A medical monitoring system increases patient safety and confidence. The system has a disposable injection device with a container holder for holding a container such as a cartridge or a syringe with a liquid drug for subcutaneous injection. The system includes a passive machine-readable tag mounted to a device housing of the injection device and coding or storing drug information about the drug in the container. The system also includes an electronic module or supplemental device releasably attachable to the injection device. The electronic module comprises injection status sensing means for monitoring a status of an injection or for tracking progress of a medication event, as well as a tag reader different from the sensing means for reading drug information from the machine-readable tag. The system includes a drug status signaling or interfacing unit for signaling to a user a drug status based on, or derived from, the drug information.

19 Claims, 2 Drawing Sheets

(52) U.S. Cl.
CPC . *A61M 2205/18* (2013.01); *A61M 2205/3553* (2013.01); *A61M 2205/3584* (2013.01); *A61M 2205/50* (2013.01); *A61M 2205/581* (2013.01); *A61M 2205/582* (2013.01); *A61M 2205/583* (2013.01); *A61M 2205/587* (2013.01); *A61M 2205/6054* (2013.01)

(58) Field of Classification Search
CPC ...... A61M 2205/3584; A61M 2205/50; A61M 2205/6054; A61M 5/3219; A61M 5/3243; A61M 5/326
See application file for complete search history.

(56) References Cited

U.S. PATENT DOCUMENTS

| | | | |
|---|---|---|---|
| 2008/0059016 | A1 | 3/2008 | Mayhew et al. |
| 2008/0200747 | A1 | 8/2008 | Wagner et al. |
| 2008/0306443 | A1* | 12/2008 | Neer ................. A61M 5/14546 604/121 |
| 2015/0182695 | A1 | 7/2015 | Rosinko |
| 2015/0201880 | A1* | 7/2015 | Bureau ................. A61M 5/158 600/301 |
| 2015/0251839 | A1 | 9/2015 | Denny et al. |
| 2015/0290396 | A1* | 10/2015 | Nagar .................... G16H 20/13 340/540 |
| 2015/0328411 | A1 | 11/2015 | Friedman |
| 2016/0074587 | A1* | 3/2016 | Searle ............... A61M 5/14248 604/189 |
| 2016/0213848 | A1 | 7/2016 | Whalley et al. |
| 2018/0369482 | A1* | 12/2018 | Pedersen ............ A61M 5/31511 |
| 2020/0078519 | A1* | 3/2020 | Helmer ................. G16H 40/63 |
| 2020/0254176 | A1 | 8/2020 | Rytz et al. |

FOREIGN PATENT DOCUMENTS

| | | |
|---|---|---|
| CN | 106345005 A | 1/2017 |
| EP | 3476417 A1 | 5/2019 |
| JP | 2009050289 A | 3/2009 |
| WO | 2015100340 A1 | 7/2015 |
| WO | 2016014365 A1 | 1/2016 |
| WO | 2016033507 A2 | 3/2016 |
| WO | 2016039298 A1 | 3/2016 |
| WO | 2016041863 A1 | 3/2016 |
| WO | 2017132577 A1 | 8/2017 |
| WO | 2017184777 A1 | 10/2017 |
| WO | 2019077482 A1 | 4/2019 |
| WO | 2019087000 A1 | 5/2019 |
| WO | 2019087001 A1 | 5/2019 |

OTHER PUBLICATIONS

International Preliminary Report on Patentability received for International Application No. PCT/IB2018/058200, dated May 5, 2020, 9 pages.
International Search Report and Written Opinion received for International Application No. PCT/IB2018/058198, dated Jan. 29, 2019, 10 pages.
International Search Report and Written Opinion received for International Application No. PCT/IB2018/058200, dated Jan. 8, 2019, 13 pages.
Extended European Search Report received for European Patent Application No. 17199307.4 dated Jun. 5, 2018, 8 pages.
Pajic, Miroslav , et al., "Model-Driven Safety Analysis of Closed-Loop Medical Systems", IEEE Transactions on Industrial Informatics, vol. 10, No. 1, pp. 3-16, Feb. 2014.

* cited by examiner

MONITORING OF DISPOSABLE INJECTION DEVICES

CROSS-REFERENCE TO RELATED APPLICATIONS

This application is a continuation of International Patent Application No. PCT/IB2018/058200, filed Oct. 22, 2018, entitled "MONITORING OF DISPOSABLE INJECTION DEVICES," which in turn claims priority to European Patent Application No. 17199307.4, filed Oct. 31, 2017, each of which is incorporated by reference herein, in the entirety and for all purposes.

FIELD OF THE INVENTION

The present invention relates to drug delivery systems for delivering, administering, injecting, infusing and/or dispensing liquids including a drug, medicament, or active ingredient. It starts from a medical monitoring system with an injection device and an electronic module attachable to the injection device.

BACKGROUND OF THE INVENTION

A variety of diseases exist that require regular treatment by subcutaneous administration of a medicament, and a number of drug delivery devices have been developed to support a patient in accurately and controllably delivering an amount of drug in a self-administration process. Delivery devices include injection devices that are removed from the injection site after each medication event or drug delivery process. Disposable injection devices include auto-injectors, patch injectors, variable dose injection pens, and any other injection device for delivering a fixed or variable dose of drug from a container that is not intended to be replaced by the patient. Fixed dose disposable injection devices include single-dose injection devices such as auto-injectors or patch injectors as well as multi-dose injection devices such as fixed dose injectors. Auto-injectors automatically deliver a fixed dose of liquid drug from a pre-filled syringe by means of a pre-tensioned injection spring provided for biasing a piston rod and advancing a piston comprised in the syringe. Patch injectors or ready-to-use, pre-filled wearable bolus injectors are attached to the skin of the patient in view of a single dose injection taking between thirty seconds and several minutes. Fixed-dose injectors have a single, non-variable dosage volume, or provide a limited number of fixed, non-variable injection dosage volumes for the user to choose from.

Diabetes may be treated by administration of insulin with the help of delivery devices that are handled by the patients themselves. Suitable delivery devices include pre-filled multi-dose disposable insulin pens as well as re-usable insulin pens that allow replacement of an empty insulin cartridge by a new one. Such variable-dose injection devices may benefit from an electronic unit or control unit integrated in the injection device, or being part of an auxiliary or supplemental module detachably attached to the injection device. The electronic unit in turn serves to monitor the injection of insulin, in order to proactively prevent false handling of the device and/or to keep track of the doses already applied. In addition to generating data related to an instantaneous condition and/or use of the injection device, information on the insulin type, cartridge batch, and/or expiration date may be evaluated by the electronic unit.

EP 17163755.6 discloses an electronic unit comprising a mechanical feedback sensor and a processor unit adapted to cooperate with an injection device generating a mechanical feedback during an injection process. The electronic unit is part of a reusable electronic module that attaches to a mechanical injection device for monitoring of an injection process executed by a user by means of the injection device. The electronic module has a dedicated module housing adapted to be attached, by means of a releasable locking mechanism, to a component or part of the injection device such as a device housing or a discharge button, and is designed to avoid obstruction of other interface elements of the injection device, specifically obstruction of a dosing knob. The electronic module is adapted to detect and exploit mechanical, tactile, and/or acoustic feedback signals emanating from the injection device. The electronic unit comprises a visual, audible and/or tactile status indicator indicating to a user a status of the system as derived from the feedback sensor output. The status of the system may include any of a device status of the injection device, a module status of the electronic module, or a process status of an overall injection process or injection device handling process. The status information may include a positive confirmation of a dose having been set or corrected, or an indication about a lapse of a minimum holding, delay, or dwell time following completion of a substance expel or piston advancing activity to inform the user that it is now safe to remove the injection device.

A wireless communication unit is connected to the processor unit, and adapted to wirelessly communicate, specifically upload, injection information to a nearby mobile device or dedicated medical gateway. The injection information includes at least a time stamp and the expelled dose, indicative of a time of a medication event and of a quantity of injected medicament, and optionally a dialed and/or corrected dose. The injection information may be transmitted instantaneously, or stored in a memory unit connected to the processor unit, for later upload or batch transfer. The injection information may, in addition or alternatively, include a quality measure of an injection process, such as a binary flag indicating that a determined dialed dose corresponds to a determined expelled dose.

WO 2001/062322 discloses a medicament dispenser such as an inhalator comprising a medicament (aerosol) container which is removably mountable in the housing of the dispenser. A Radio Frequency Identification (RFID) tag moulded into the housing of the dispenser includes an antenna and an integrated circuit chip connecting with said antenna. The RFID tag is arranged for reading of data therefrom by a reader remote from the medicament dispenser, such as a hand-held/portable electronic device, by transmitting radiofrequency energy to the antenna and receiving radiofrequency energy therefrom. The reader is arranged to communicate with a local electronic data management system or a networked computer system, and to write information to the RFID tag once a specific step in the process has been completed.

In the context of a medical self-administration process, reading and writing of an RFID tag, specifically of a Near-Field Communication (NFC) tag, by a mobile device may be problematic because of the limited provision and/or accessibility of RFID interfaces in current mobile devices and because of the inherent limitation of the communication range. After an initial pairing and exchange of power and information between the target delivery device with the RFID tag and the mobile device with the initiator RFID transceiver, the two devices are likely to separate for the rest of the injection process. Accordingly, for control or documentation purposes, specifically for writing of changed information to the RFID tag at the end of the injection, the two devices have to be brought into contact again at the end of the medication event. This may be forgotten by a patient.

WO 2009/024562 discloses a medical device with a Radio Frequency Identification (RFID) unit comprising a pressure sensor integrated with a liquid medicament container to enable wireless pressure monitoring. The liquid medicament container is coupled with a first housing part of the medical device, which first housing part may for instance constitute a pre-filled disposable injection device. The RFID unit communicates wirelessly with a control circuit that is contained in a second housing part of the medical device, or in an associated auxiliary module that is releasably attached to the first housing part. The control circuit is adapted to process the values measured by the RFID unit, to compare these with pre-defined values and to provide an alert to the user if the measured values fall outside of normal operating conditions, and to communicate data relating to the measured values to an external computing device for further data processing.

Alternatively, the auxiliary module of WO 2009/024562 holds a control circuit which includes a power supply, a radiofrequency transmitter and receiver and antenna means for sending and receiving electromagnetic radiation to power a passive RFID sensor system of the injection device so that the sensor system is able to pick up sensed data regarding various conditions of the injection device such as movements of the actuator mechanism. The sensor system is integrated with the drug cartridge or arranged in the vicinity of the actuator mechanism, and may additionally be utilized for encoding the type of drug or cartridge, and/or information about a production date. Accordingly, the medical delivery device may receive the coded information and derive for instance whether the drug is the one programmed in the medical device for the user to use, or whether the recommended last usage date has expired.

Attaching an RFID tag to a container that is subsequently inserted into a delivery device may be problematic as the space or radial distance between the container and the inner surface of a container holder may become very small due to unavoidable manufacturing tolerances. This may lead to damage such as partial detachment of a tag including an antenna and sensors during insertion of the container into the container holder. Either the diameter of the container or of the container holder may have to be, at least locally, adapted to accommodate for a tag that is less two-dimensional than a mere paper label. Likewise, arranging a tag in the vicinity of an actuator mechanism for sensing movements of the latter requires a device design specifically adapted. However, changes to the internal design of the injection device generally have major consequences and definitely are not feasible in retrofit configurations with an existing and proven injector design.

In the present context, the terms "substance", "drug", "medicament" and "medication" are to be understood to include any flowable medical formulation suitable for controlled administration through a means such as, for example, a cannula or a hollow needle, and comprises a liquid, a solution, a gel or a fine suspension containing one or more medically active ingredients. A medicament can be a composition comprising a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from, or harvested by, biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances.

DESCRIPTION OF THE INVENTION

It is an objective of the invention to increase patient safety and confidence in a medical monitoring system with an electronic module attachable to an injection device for monitoring purposes. This objective is achieved by a medical monitoring system and by an electronic module and a method according to the independent claims. Various embodiments are evident from the dependent patent claims.

According to the invention, a medical monitoring system includes a disposable injection device with a container holder for holding a container or reservoir such as a cartridge or a syringe comprising a liquid drug for subcutaneous or intramuscular injection. The system further includes a passive machine-readable tag mounted to, for instance embedded in or attached to a surface of, a device housing of the injection device and coding or storing drug information about the drug comprised in the container. The system also includes an electronic module or supplemental device adapted to be releasably, or reversibly, attached to the injection device. The electronic module comprises injection status sensing means for monitoring a status of an injection or for tracking a progress of a medication event, as well as a tag reader different from the sensing means for reading the drug information from the machine-readable tag. The system additionally includes a drug status signaling or interfacing unit for signaling to a user a drug status that is based on, or derived from, the drug information.

The disposable injection device preferably may be an auto-injector, a patch injector, a variable dose injection pen, or any other injection device for delivering a fixed or variable dose of a drug from a container that is not intended to be replaced by the patient. The injection device may be automated and comprise a preloaded mechanical or even electrical source of energy for expelling the drug, or be exclusively powered by the self-administrating patient. Even in the presence of a source of electrical power in the injection device the use of a separate electronic module may be advantageous, not least in retrofit configurations with an existing injection device design that is not adaptable for the inclusion of sensors and electronics.

The injection status sensing means of the electronic module capture signals indicative of an injection status that depends on a position or a movement of a component of the injection device. The injection status may include a device status of the injection device or a process status of an overall medication event or injection device handling process. The machine readable tag may be devoid of any sensing capability or other dynamic interaction with the interior of the injection device. The injection device does not have to, and in embodiments may not, include sensing and signaling electronics on behalf of a device-external receiver, in agreement with a requirement for reverting to existing and proven injection device designs. Mounting the tag to the injection device housing specifically excludes attaching the tag to the drug container. Accordingly, both the machine-readable tag and the tag reader of the electronic module may be arranged proximal of a proximal end of the container and/or of a container viewing window of an elongated, pen-shaped injection device, with the term "proximal" referring to a location or direction associated with the end of the injection device that is opposite a distal end, wherein the distal end comprises a needle or cannula.

The drug information includes any or all of a drug identifier, an expiry date, or a batch number of the drug, medicament, or active ingredient contained in the container. The drug information traditionally may have been included in a barcode or plain text Unique Device Identifier. The status may be derived from the drug information as previously obtained from the machine-readable tag by an evaluating processor unit, preferably in relation to or in connection with further evaluation information. For instance, coded drug information about the drug type may be compared by the processor unit with a therapy plan of the patient and/or with stored information about previous administrations, to develop drug information confirming that drug type, or placebo in case of a clinical trial phase, and drug dose identified and ready to be injected are indeed the correct medication to be administered imminently. This may constitute particularly valuable monitoring information in case of multiple drug types or medication variants being scheduled for alternating administration by the patient, specifically if such multiple drugs are administered by way of identical or similar injection devices. Further, coded drug information may include a number or identifier of the batch or lot to which the instant container pertains, which may be evaluated against information indicative of a possible recall of the batch in question. Additionally, drug information about the expiry date of the drug comprised in the container may be evaluated against the actual date. In the event of wrong medication, batch recall, or drug expiration a corresponding alarm is signalled to the user by the signalling unit, whereas in the absence of such event, either no signal or a safe-to-use signal is emitted following evaluation. The invention thus contributes, by way of a confirmatory or warning feedback after evaluation in due time prior to injection, to an increased confidence of the patient in what he or she is expected to be doing, to fewer handling errors, and additionally to an increased adherence to a therapy plan. Furthermore, the medical monitoring system according to the invention allows to easily and unambiguously complement, or correlate, the monitoring results obtained by the electronic module with drug information read from the tag.

In an exemplary application, the injection device is an auto-injector, and the medical monitoring system is used in the context of a clinical trial, with all advanced remote adherence tracking being accomplished by the electronic module. In line with the invention, the electronic module may after evaluation alert users at the point-of-use in case a batch of investigational drug distributed earlier has to be corrected or removed from the clinical trial. In this context, automated handling and evaluation of drug information read from the tag reduces the number of system interaction steps that the trial patient is expected to perform, including monitoring of drug supply, and minimizes the administrative burden of conducting and documenting clinical research. With all monitoring, documenting and supporting functionality being executed by the electronic module, the auto-injector itself does not require any physical modification, and the same auto-injector can be used for the clinical trials as well as for the commercial drug product.

In implementations and alternatives the electronic module includes the evaluating processor unit to evaluate the drug information read from the tag, as well as the signaling unit. In this case the further evaluation information has to be available at the electronic module locally, which may imply a local clock and/or a memory unit storing a copy of the therapy plan or drug batch information in the form of a blacklist or a whitelist. The latter obviously has to be preloaded to the memory unit beforehand. The memory unit may also store information about previous medication events of the injection device.

Any signaling unit of the electronic module, whether for signaling a drug status evaluated locally or received by a communication unit of the electronic module, comprises a visual, audible and/or tactile status indicator as the human machine interface (HMI) or interfacing means. The status indicator may be simple and limited to a multicolor LED or to no more than three distinct LEDs in traffic-light colors and/or an audible signal generator for generating language-independent beep sounds or simple melodies. The status indicator may explicitly exclude any advanced human-machine interfacing capability, and be limited to a few, specifically less than ten, messages conveyable to the user. In particular, the electronic module may be devoid of a display, screen, or projector for visually transmitting readable instructions, and likewise exclude an artificial speech assistant for reading out loud the instructions. Such advanced HMI functionality including elaborate graphic display and speech output capabilities are preferably being provided by a mobile device communicatively connected to the electronic module.

In implementations and alternatives, the system comprises a gateway device, specifically a stationary internet or medical gateway device, communicatively connected to a remote server, and adapted to retrieve the most updated evaluation information therefrom. The electronic module comprises a communication unit to transmit the drug information to the gateway device, and to receive the evaluation information from the gateway device. Specifically, an updated batch recall or safe-to-use condition of a batch may be provided by the server upon receipt of the batch number read from the tag, and transmitted via the gateway device to the evaluating processor unit of the electronic module. In this case, less or no evaluation information has to be stored at the electronic module. With the attention of the user being tied to the electronic module, the gateway device does not need to, and in implementations and alternatives may not, include an elaborate HMI.

In implementations and alternatives, the electronic module comprises a communication unit to transmit the drug information to a mobile device such as a smartphone or tablet device running a dedicated application program, or a laptop computer configured accordingly. The mobile device in turn comprises the evaluating processor unit to derive the drug status based on the drug information. The drug status may be signaled to the user by an elaborate HMI of the mobile device, or returned to the electronic module for signaling by a signaling unit of the electronic module as described above. The latter may be beneficial as the focus of the patient may be on the injection device and hence on the signaling unit of the electronic module rather than on the mobile device.

In implementations and alternatives, the mobile device is in turn communicatively connected to a remote server, and adapted to retrieve the most updated evaluation information therefrom, to be evaluated by the evaluating processor unit of the mobile device. Specifically, an update about a batch recall or safe-to-use condition of a batch may be obtained upon receipt of the batch number and transmitted to the mobile device.

Communication between the electronic module and the gateway device or the mobile device may take place via Bluetooth Low Energy (BTLE) or equivalent short or near range wireless communication technology. In this context it is understood that a potential tag reading unit of the gateway or mobile device is not used to access the drug information of the tag, and that any restriction as to a relative arrangement of the gateway or mobile device and the injection device is determined by the communication technology employed by the communication unit of the electronic module.

In implementations and alternatives, the machine-readable tag is attached externally to the device housing, which is compatible with non-transparent device housings, and which specifically excludes embedding the tag into the device housing in a manufacturing or molding step of the device housing preceding an assembly of the injection device. Attaching the tag to the device housing surface allows delaying of a programming or printing of the tag to a very late stage, specifically to finalize the tag during or even after assembly of the drug container and the injection device, but still before attachment of the tag to the device housing.

The passive machine-readable tag may include an optical bar code or a data-matrix/QR code, or even a portion of plain text printed on an adhesive label, that may be scanned by the electronic module by means of a corresponding bar code or QR code reading unit, or by an OCR unit, preferably during a relative displacement or approach of the tag and the reader. However, optical tags may become unreadable through scratches or deposits and are not designed to be rewritten or otherwise modified, and corresponding reading units tend to be complex and/or expensive. Therefore a non-optical Radio Frequency Identification (RFID) tag or transponder may be employed, specifically a NFC tag operating according to one of the Near-Field Communication (NFC) standards. Accordingly, the electronic module is equipped with an RFID/NFC reading or readout unit. Such a drug-information RFID reading unit may be used concurrently for reading of sensor signals provided from an appropriate RFID transponder, either separate from or identical with the aforementioned drug-information carrying tag. For instance, a temperature sensor for determining that a target temperature for injection has been reached may be implemented as a single-chip RFID field-powered temperature sensor mounted to the injection device. This temperature feedback further contributes to an increased ease and confidence of the patient.

At least the standardized Near-Field Communication (NFC) tags contain data including unique tag identifiers such as serial numbers encoded in the tag at the time of manufacture in read-only format such that this information cannot be altered once set, as well as a section for rewriteable information. A user memory in a tiny chip of a up to a few hundred bytes provides for sufficient space to store the drug information even in the presence of adequate cyber security measures. They can be custom-encoded by their manufacturers. Near-field communication uses magnetic induction between two loop antennas connected to respective RFID chips or control units, and located within a near field of each other, thus effectively forming an air-core transformer operating at an exemplary frequency of 13.56 MHz well below an UHF band of 300 MHz or higher. There are two communication modes, passive and active mode. In the passive communication mode, the initiator device provides a carrier field and the target device responds by modulating the existing field. In this mode, the target device may draw its operating power from the initiator-provided electromagnetic field. In the context of the present invention, the initiator is an electronic unit as part of the electronic module, and the target is the passive tag or transponder attached to the medicament delivery device housing. In the active communication mode, both initiator and target device communicate by alternately generating their own fields. A device deactivates its RF field while it is waiting for data. In this mode, both devices typically have power supplies.

The RFID tag may be an inlay embedded in a smart label between a layer of adhesive and an outmost layer carrying printed text. Alternatively, the RFID tag may itself include some adhesive to be attached to the device housing, specifically to a part of the external surface of the device housing forming a recess or shallow depression of a depth corresponding to the thickness of the RFID tag, in order to be covered subsequently by an ordinary text label or sticker. Instead of a recess, a wall extending from the device housing surface and essentially surrounding the tag may be provided to prevent mechanical contact between the tag and the electronic module housing.

In further implementations and alternatives, the RFID tag comprises a re-writable memory section, and the electronic module comprises an RFID writer to write changed drug information to the re-writable memory section of the RFID tag. Changed drug information may relate to a medication event having been completed recently, and include binary information indicative of the completion, timing information indicative of the date and time of the completion, quantitative information indicative of the expelled dose, qualitative information indicative of an expelled dose matching a dialed dose, or of an observed holding time being sufficient. Changed information may include any other kind of information that may be of value at a later stage, such as when reading the RFID memory section of disposed-of injection devices for post injection studies. Specifically, in case the injection device is a multi-dose device, the evaluating processor unit may be configured to determine, from a dose of drug ejected and measured by the sensing means, an amount of drug remaining in the container. This amount is written to the RFID tag, and may serve as drug information for subsequent medication events. Storing certain re-writable information on the device itself lowers complexity of data management, at least until the injection device is disposed of, and specifically in case of multiple electronic modules or mobile devices being used with one and the same injection device.

According to another implementation, an electronic module or supplemental device adapted to be detachably attached to a device housing of a disposable injection device comprises injection status sensing means for monitoring a status of an injection or for tracking a progress of a medication event performed by means of the injection device. The electronic module comprises a tag reader for reading or capturing drug information that is stored on a machine-readable tag mounted to the device housing. The electronic module further comprises a wireless communication unit for communicating drug information read from the tag to a nearby mobile device or medical gateway. The drug information stored in the tag may include a batch number of a drug comprised in a container having been inserted into the injection device to which the module is attached.

The injection status sensing means may include a mechanical feedback sensor and a processor unit adapted to cooperate with an injection device generating a tactile or acoustic feedback during a medication event. The injection status sensing means may include an electrical sensor such as a contact-free inductive or capacitive sensor. An exemplary inductive sensor may detect initial, intermediate, and final values of, and/or corresponding changes or differences in, a static or alternating magnetic field or flux depending on a position or displacement of a magnetic device component. The injection status may include a device status of the injection device or a process status of an overall medication event or injection device handling process, and may also be communicated or uploaded by the communication unit.

In another implementation, the electronic unit comprises drug status signaling means for signaling a drug status evaluated from the drug information. An evaluating processor unit, either being part of the electronic module and receiving additional evaluation information in response to the drug information having been communicated, or being part of a mobile device receiving the drug information, prepares, and eventually returns, the evaluated drug status in the form of a safe-to-use feedback to be signalled by the signalling unit.

In a further implementation, the tag is a Radio-Frequency Identification (RFID) tag, and the tag reader is adapted to read a passive RFID tag containing electronically stored drug information and being mounted to a device housing of the injection device. The RFID reader is different from or additional to the injection status sensing means. Correspondingly, the RFID tag is devoid of any sensing capability or other dynamic interaction with the interior of the injection device, and the injection device is devoid of sensing and signaling electronics.

BRIEF DESCRIPTION OF THE DRAWINGS

The subject matter of the invention will be explained in more detail in the following text with reference to exemplary embodiments which are illustrated in the attached drawings, in which.

The reference symbols used in the drawings, and their primary meanings, are listed in summary form in the list of designations. In principle, identical parts are provided with the same reference symbols in the figures.

DETAILED DESCRIPTION OF EMBODIMENTS

Figure 1:
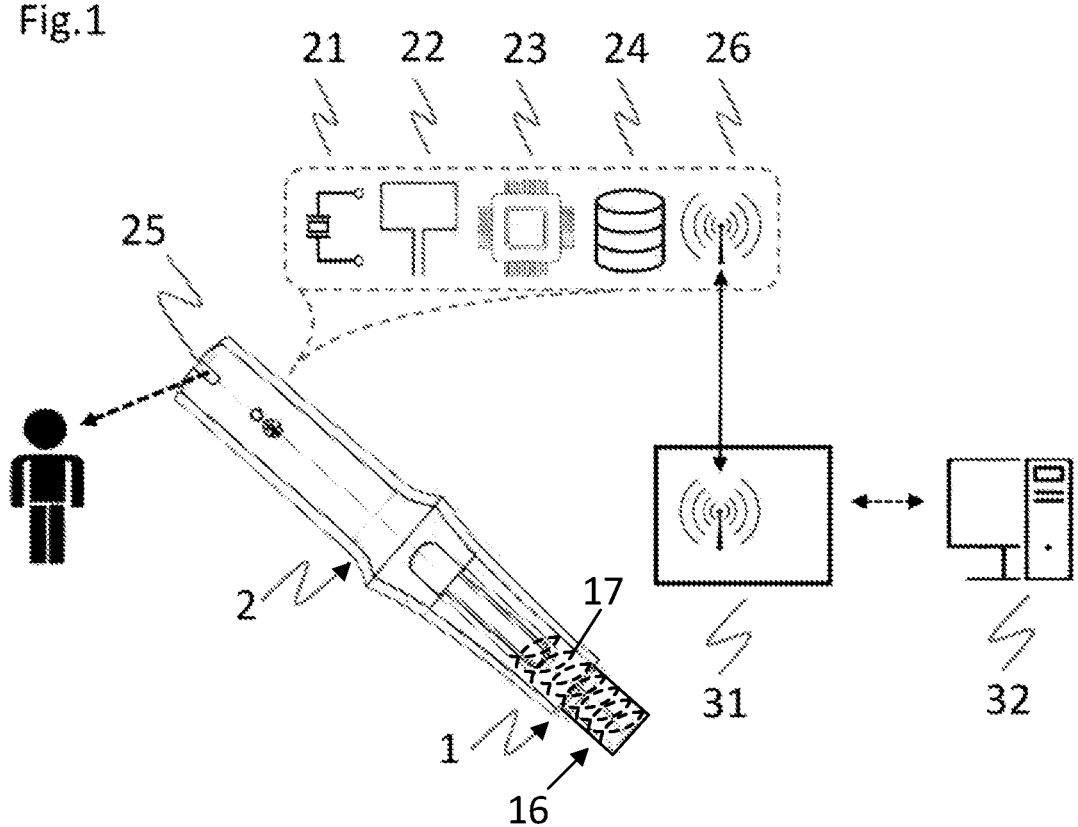
FIG. 1 depicts a variant of a medical monitoring system and method with an auto-injector.

FIG. 1 depicts a variant of a medical monitoring system, comprising an auto-injector as an exemplary disposable injection device 1, an electronic module 2 releasably attached to a device housing of the injection device, and an optional gateway device 31 communicatively connected via a data communication network 33, e.g., the Internet, to a remote server, cloud based computing facility, or expert system 32. The electronic module 2 comprises an electrical or mechanical feedback sensor as injection status sensing means 21, as well as a tag reader 22 for reading drug information from a tag or label mounted to, or supported by, the device housing. The electronic module 2 further comprises an evaluating processor unit 23 for evaluating the drug information and for deriving a drug status therefrom. A memory or data storage unit 24 may store evaluation information on behalf of the evaluating unit. The electronic module 2 further includes a multicolor LED as a drug status signaling means or interfacing unit 25 for providing visual feedback about the drug status, and optionally about an injection status such as a progress of an ongoing injection process, or about an availability of battery power. A communication unit 26 for wireless transmission of drug information and communication of evaluating information to and from the optional gateway device 31 via Bluetooth Low Energy (BTLE) or equivalent short or near range wireless communication (NFC) technology may further be provided.

Included in the module housing is a lock/release mechanism to secure the attachment of the electronic module 2 to the injection device 1 in order to protect against unintended detachment, specifically during removal of a needle protective cap from the auto-injector. The auto-injector 1 is intended for automatically delivering a fixed dose of liquid drug from a pre-filled syringe by means of a pre-tensioned injection spring provided for biasing a piston rod and advancing a piston comprised in the syringe. The auto-injector 1 comprises a needle protective sleeve 16, or cover sleeve, for protecting a needle of the syringe after removal from the injection site. Upon removal of the auto-injector from the injection site the needle protective sleeve 16 is biased to a needle protecting position by a cover sleeve spring 17, and locked in this position by a locking means generating a locking sound. Start and end of a substance delivery as well as injection device lift-off may be detected by the injection status sensing means 21 and advantageously combined to obtain a characterization of the ongoing injection process or medication event, in order to track whether an injection event has occurred according to the medication schedule but also whether that injection event was successfully completed or not.

The electronic module 2 of FIG. 1 has a rear, or proximal, part where some or all electronic components as described are located. With the tag reader 22 being arranged in this proximal part, the machine-readable tag is beneficially mounted to a proximal end surface of the injection device 1, perpendicular to a longitudinal main axis and adjacent to the tag reader 22. As this end surface hitherto has remained unused, introduction of an extra tagging or labeling step during device manufacture is necessary. In case of an RFID transponder with an antenna attached to the end surface, inductive components inside the auto-injector, such as the metallic injection or cover sleeve springs 17, may interfere with the RFID antenna. Still in case of an RFID reader, an antenna of the electronic module 2, oriented parallel and adjacent to the RFID transponder antenna may have to be shielded from the further electronic components of the electronic module 2. From an electromagnetic coupling point of view, arranging the antennas at right angles, with one antenna perpendicular and the other antenna parallel to the main axis, is not excluded.

Figure 2:
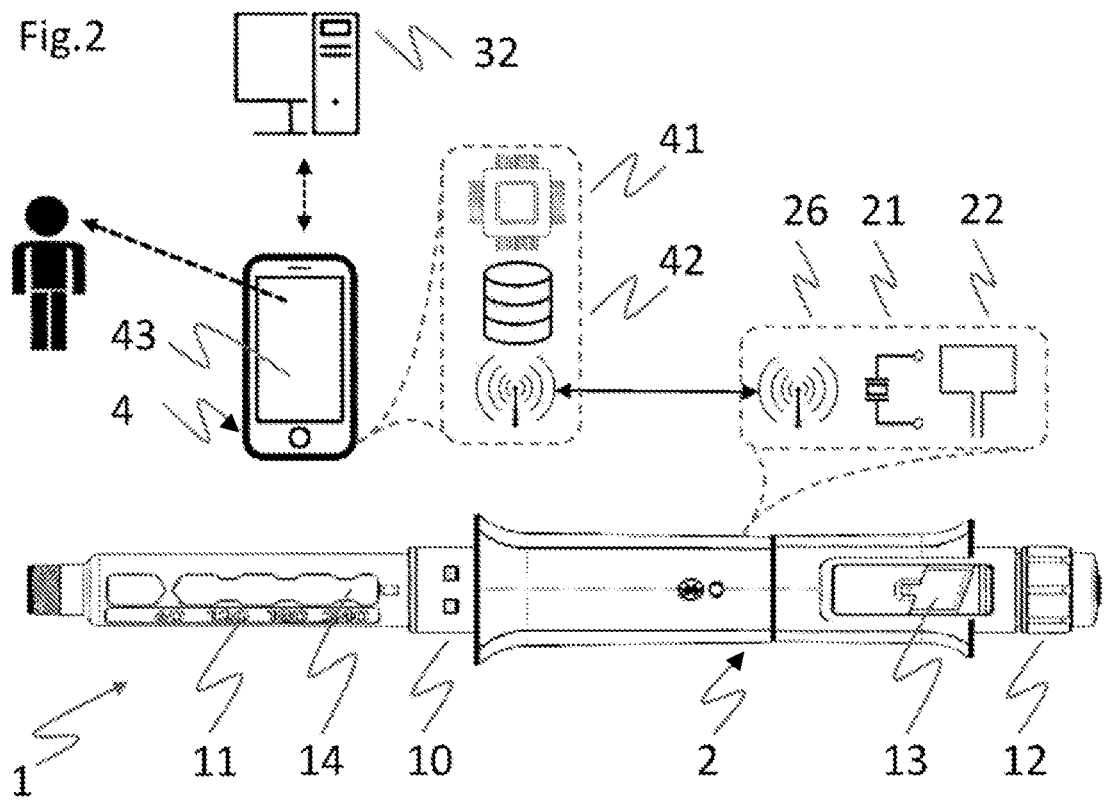
FIG. 2 depicts another system and method with a variable dose injection device and a mobile device.

FIG. 2 depicts a variant of a medical monitoring system, comprising a variable dose injection device 1 with a dose dialing facility as amply described for instance in EP 2812055, an electronic module 2 and a mobile device 4, such as a smartphone or tablet device running a dedicated application program, or a laptop computer configured accordingly. The mobile device 4 is optionally adapted to interact with a remote server, cloud based computing facility, or expert system 32. The electronic module 2 comprises an electrical or mechanical feedback sensor as injection status sensing means 21, a tag reader 22 for reading drug information from a tag mounted to the device housing, and a communication unit 26 for wireless transmission of drug information to the mobile device via Bluetooth Low Energy (BTLE) or equivalent short or near range wireless communication (NFC) technology. The mobile device 4 includes an evaluating processor unit 41 for evaluating the drug information and for deriving a drug status therefrom. A memory or data storage unit 42 may store evaluation information on behalf of the evaluating processor unit 41. The elaborate HMI facilities of the mobile device serve as drug status signaling means 43 for providing visual, tactile, acoustical feedback about the drug status, and optionally about an injection status such as progress of an ongoing injection process. The device housing 10 of the pen-shaped injection device 1 is fixed to a cartridge holder 11 containing a cartridge as a transparent container filled with a liquid drug. The cartridge holder 11 has a container viewing window 14 permitting visual access to the liquid drug. A dosing sleeve and a rotary dosing knob 12 for enabling the user to adjust a dose are arranged on the proximal end of the injection device. When the dosing sleeve is screwed out of the housing during the dosing operation, the adjusted dose is displayed in a dose display window 13. On the proximal end of the injection unit, a discharge button is snapped on the dosing sleeve.

The electronic module 2 of FIG. 2 has an essentially tubular module housing that, when properly slid over the injection device housing, surrounds the injection device 1 in a position such as to neither interfere with the dial-and-dose components 12 nor obscure a dose display window 13 of the device. This requirement obviously excludes providing the tag at a proximal end surface as in the previous variant. To this purpose, the module housing has a recess or cut-out that matches with the dose display window 13. Hence the patient may continue using the injection device in a known manner, despite the presence of the electronic module, with all device interface elements remaining fully accessible throughout the handling sequence. On the other hand, the electronic module 2 may also include a mechanical sensor to mechanically detect a rotation angle or linear shift of the dosing knob, or an optical sensor to read a dialed dose from a dosing sleeve.

Figure 3:
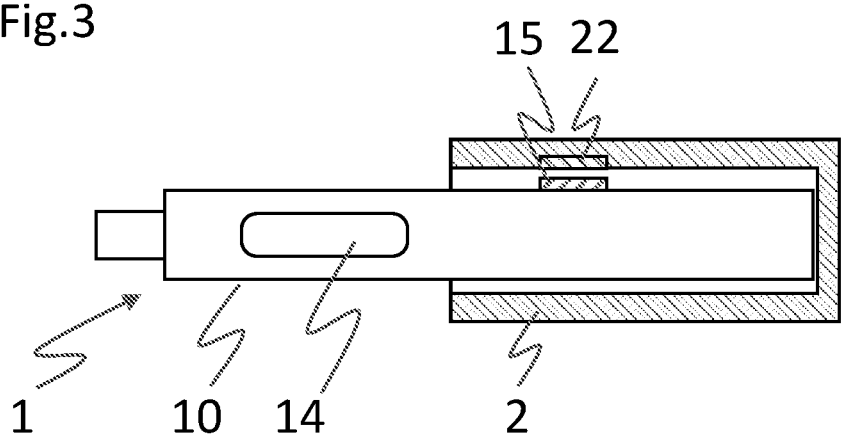
FIG. 3 depicts an axially aligned arrangement of an RFID tag and an RFID tag reader.

FIG. 3 depicts in simplified form an axially aligned arrangement of an RFID tag, specifically of the corresponding transponder antenna, 15 on ejection device 1 and an RFID tag reader or corresponding reader antenna 22 of electronic module 2, applicable to both preceding variants. An injection device 1 with a device housing 10 and a container viewing window 14 is partly surrounded by electronic module 2. The latter as well as the RFID tag antenna 15 and the RFID tag reader antenna 22 are depicted in a cross-sectional view. The antennas include a circular or rectangular conductor loop or spiral with an area of preferably less than 20×20 mm, printed on a circuit board or on a flexible support. The tag 15 is attached to a longitudinal external surface of the device housing 10, and axially positioned opposite of, in a transversal direction, the tag reader 22. The tag reader 22 in turn is attached to a recess of a module housing of the electronic module 2. In an axial direction, the tag 15 is attached to a proximal part of the device housing 10 proximal of the container viewing window 14 and/or the container, such that the tag and the reader may axially overlap without the electronic module 2 obstructing the container viewing window 14 when attached to the injection device 1 in an axially fixed position.

Figure 4:
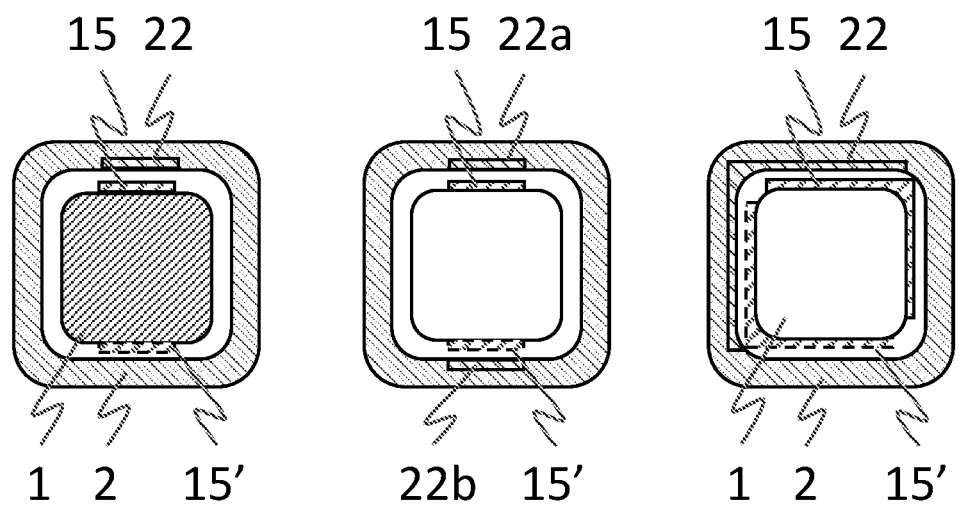
FIG. 4 depicts three transversally distinct arrangements of the tag and the tag reader.

FIG. 4 depicts three cross-sectional views of an injection device 1 and an electronic module 2 surrounding the injection device, each with a transversally distinct arrangement of an RFID tag/antenna 15 and an RFID tag reader 22. In the RFID case the antenna of the RFID tag/transponder and the antenna of a RFID reader are generally arranged as close as possible to each other such that an optimal inductive coupling is permanently achieved in a coupled state of injection device 1 and electronic module 2. Hence in a transversal direction, misalignment or even rotation of the electronic module around the injection device has to be at least partly prevented, or the antennas have to be arranged to account for such misalignment or rotation. Rotation is prevented by a non-rotational axial symmetry as exemplified by the square-shaped cross sections in FIG. 4. However, misalignment may still occur as two different orientations of the electronic module with respect to the injection device are still assumed possible, i.e., the electronic module 2 may be turned 180° around the longitudinal axis and still fit to the injection device 1. In this case, a single reader antenna 22 and a single transponder tag/antenna 15 may be provided with optimized range, allowing to read a misaligned tag/antenna 15' even across the injection device at a distance of approximately 20 mm that is comparable to the lateral dimensions of the antennas (leftmost drawing). Due to the increased range or sensitivity of the tag reader 22, an electromagnetic shield may be needed against RF signals from outside of the system. Alternatively, two tag/reader antennas 22a, 22b may be provided at opposite sides of the electronic module 2, such as to optimize the coupling with a single transponder antenna 15, 15' in both orientations (center drawing). This solution may require additional space in the electronic module, but avoids the drawbacks related to alien signals. Further alternatively, both a single reader antenna 22 and a single tag/transponder antenna 15, 15' are arranged to cover two adjacent sides of the module housing and the device housing, respectively (right-hand drawing). Here the antenna loops may include a kink along a center line interconnecting two perpendicular antenna loop halves. In this case a loop half of the reader antenna 22 is adjacent a loop half of the transponder antenna 15, 15', whatever the orientation of the electronic module 2.

While the invention has been described in detail in the drawings and foregoing description, such description is to be considered illustrative or exemplary and not restrictive. Variations to the disclosed embodiments can be understood and effected by those skilled in the art and practising the claimed invention, from a study of the drawings, the disclosure, and the appended claims. In the claims, the word "comprising" does not exclude other elements or steps, and the indefinite article "a" or "an" does not exclude a plurality. The mere fact that certain elements or steps are recited in distinct claims does not indicate that a combination of these elements or steps cannot be used to advantage, specifically, in addition to the actual claim dependency, any further meaningful claim combination shall be considered disclosed.

LIST OF DESIGNATIONS

1 Injection device
10 Device housing
11 Cartridge/container holder
12 Dosing knob
13 Dose display window
14 Container viewing window
15, 15' Tag/transponder with antenna
2 Electronic module
21 Sensing means
22 Tag reader with antenna
23, 41 Evaluating processor unit
24, 42 Memory unit
25, 43 Signalling means
26 Communication unit 31 Gateway device
32 Remote server
33 Network
4 Mobile device

The invention claimed is:

1. A medical monitoring system comprising:
an injection device configured as a disposable auto-injector or a disposable fixed or variable dose injection pen for patient self-administering with an injection device housing coupled to a container holder for holding a container with a liquid drug, the injection device housing comprising,
a needle protective sleeve at a distal end biased by a metallic cover sleeve spring configured as a magnetic device component; and
a machine-readable tag with drug information on the liquid drug, the tag mounted to a proximal part of the injection device housing and arranged proximal to a container viewing window of the container holder, wherein the drug information comprises information selected from: a drug identifier, an expiry date, a batch number or batch identifier of the drug, a medicament or active ingredient contained in the liquid drug, or combinations of the preceding; and
an electronic module for removable attachment to the injection device housing, the electronic module comprising:
an inductive sensor, wherein the sensor senses a change in magnetic field of the metallic cover sleeve spring corresponding to a change in position of the magnetic device component of the injection device or a movement of the magnetic device component of the injection device indicative of an injection status; and
a tag reader for reading the drug information from the machine-readable tag, wherein the tag reader overlaps with the tag without the electronic module obstructing the container viewing window when attached to the injection device housing; and
drug status signaling means for signaling a drug status based on the read drug information.

2. The medical monitoring system of claim 1, wherein the electronic module comprises:
an evaluating processor unit to derive the drug status based on the drug information, and
the drug status signaling means for signaling the derived drug status.

3. The medical monitoring system of claim 1, further comprising:
a gateway device to facilitate communication with a remote server, wherein the electronic module is adapted to transmit the drug information to the gateway device, and wherein the gateway device is configured to retrieve evaluating information from the remote server and to return the evaluating information to the electronic module.

4. The medical monitoring system of claim 1, further comprising a mobile device with an evaluating processor unit to derive the drug status based on the drug information, and wherein the electronic module is adapted to transmit the drug information to the mobile device.

5. The medical monitoring system of claim 4, wherein the mobile device is adapted to communicate with a remote server and configured to retrieve evaluating information from the remote server.

6. The medical monitoring system of claim 1, wherein the machine-readable tag is an RFID tag, and wherein the electronic module comprises an RFID reader.

7. The medical monitoring system of claim 6, wherein the RFID tag has a rewritable section, and wherein the electronic module is adapted to write information about the injection status sensed by the inductive sensor.

8. The medical monitoring system of claim 7, wherein:
the injection device is a multi-dose injection device, and
the electronic module is adapted to determine a dose delivered and to write an amount of drug remaining in the container to the rewritable section of the RFID tag.

9. The medical monitoring system of claim 1, wherein the drug status comprises information selected from: information based on comparison with or evaluation against a therapy plan of a patient, on stored information about previous administrations of a drug, on a number or identifier of a batch to which an instant container pertains, on information indicative of a possible recall of the batch in question, with drug batch information in the form of a blacklist or a whitelist, or on combinations of the preceding.

10. The medical monitoring system of claim 1, wherein the change in position or the movement of the magnetic device component corresponds to one or more of: a start of liquid drug delivery, an end of liquid drug delivery, or a movement of the needle protective sleeve by the metallic cover sleeve spring to a needle protecting position.

11. An electronic module for monitoring of an injection device configured as a disposable auto-injector or a disposable fixed or variable dose injection pen for self-administrating with an injection device housing having magnetic device component configured as a metallic cover sleeve spring biasing a needle protective sleeve at a distal end of the injection device housing, the injection device housing coupled to a container holder for holding a container with a liquid drug, the electronic module comprising:
a tubular housing configured for removable attachment to the injection device housing of the auto-injector or injection pen, the tubular housing comprising an inductive sensor, a tag reader, and a communication unit,
wherein the inductive sensor senses a change in magnetic field of the metallic cover sleeve spring corresponding to a change in position of the magnetic device component of the injection device or a movement of the magnetic device component of the injection device indicative of an injection status,
wherein the tag reader for reading drug information on the liquid drug from a machine-readable tag mounted to a proximal part of the injection device housing, wherein the electronic module is configured such that the tag reader overlaps with the tag without the electronic module obstructing a container viewing window of the container holder when attached to the device housing, and
wherein the communication unit is for communicating the read drug information.

12. The electronic module of claim 11, further comprising a drug status signaling means for signaling a drug status evaluated from the drug information.

13. The electronic module of claim 11, wherein the tag reader is an RFID tag reader.

14. The electronic module of claim 11, further comprising:
an evaluating processor unit to derive a drug status based on the drug information.

15. A medical monitoring method for monitoring use of an injection device configured as a disposable auto-injector or a disposable fixed or variable dose injection pen for self-administrating with a device housing including a needle protective sleeve at a distal end biased by a metallic cover sleeve spring configured as a magnetic device component, the device housing coupled to a container holder for holding a container with a liquid drug, the method comprising:

provided a machine-readable tag with drug information about the liquid drug mounted to the device housing;

attaching an electronic module removably to the device housing by sliding the device housing into a tubular housing of the electronic module, wherein the tubular housing comprises an inductive injection status sensor and a tag reader;

sensing, with the inductive injection status sensor of the electronic module, a change in the magnetic field of the metallic cover sleeve spring corresponding to a change in a position of the magnetic device component of the injection device or a movement of the magnetic device component of the injection device indicative of an injection status to be monitored;

activating the tag reader of the attached electronic module for reading the drug information from the tag, wherein the tubular housing of the electronic module is configured such that the tag reader overlaps with the tag without the electronic module obstructing a container viewing window of the container holder when attached thereto; and signaling to a user of the device a drug status based on the read drug information.

16. The method of claim 15, wherein the drug information comprises information selected from: a drug identifier; an expiry date; a batch number or batch identifier of the liquid drug, a medicament or active ingredient contained in the drug, or combinations of the preceding and the drug status comprises information selected from information based on comparison with or evaluation against a therapy plan of a patient, on stored information about previous administrations of a drug, on a number or identifier of a batch to which an instant container pertains, on information indicative of a possible recall of the batch in question, with drug batch information in the form of a blacklist or a whitelist, or on combinations of the preceding.

17. The method of claim 15, wherein the signaling to a user a drug status comprises one or more of:

signaling to a user with drug status signaling means of the electronic module after processing of the drug information by an evaluating processor unit of the electronic module;

signaling to a user with a human machine interface (HMI) of a mobile device after the electronic module communicates the drug information to the mobile device and processing of the drug information into a drug status by an evaluating processor unit of the mobile device; or signaling to a user by a signaling unit of the electronic module, after processing of the drug information into a drug status by the evaluating processor unit of the mobile device, wherein the mobile device returns the drug status to the electronic module after processing.

18. The method of claim 15 further comprising wirelessly transmitting from a communication unit of the electronic module drug information and reception of evaluating information to and from a gateway device via Bluetooth Low Energy (BTLE) or equivalent short or near range wireless communication (NFC) technology.

19. The method of claim 15, wherein the machine readable tag comprises an RFID tag with a rewritable section and further comprising activating the tag reader to write information into the RFID tag for later reading.

* * * * *